US005785989A

United States Patent [19]

Stanley et al.

[11] Patent Number: 5,785,989

[45] **Date of Patent: *Jul. 28, 1998**

[54] COMPOSITIONS AND METHODS OF MANUFACTURING OF ORAL DISSOLVABLE MEDICAMENTS

[75] Inventors: Theodore H. Stanley, Salt Lake City; Brian Hague, West Valley City, both of Utah

[73] Assignee: University Utah Research Foundation, Salt Lake City, Utah

[ * ] Notice: The term of this patent shall not extend beyond the expiration date of Pat. No. 5,288,497.

[21] Appl. No.: 822,560

[22] Filed: Mar. 19, 1997

Related U.S. Application Data

[63] Continuation of Ser. No. 333,233, Nov. 2, 1994, abandoned, which is a continuation of Ser. No. 152,396, Nov. 12, 1993, abandoned, which is a division of Ser. No. 403,751, Sep. 5, 1989, Pat. No. 5,288,497, which is a continuation-in-part of Ser. No. 60,045, Jun. 8, 1987, Pat. No. 4,863,737, which is a continuation-in-part of Ser. No. 729,301, May 1, 1985, Pat. No. 4,671,953.

[51] Int. Cl.[6] .......... A61K 9/68

[52] U.S. Cl. .......... 424/440; 424/439; 424/441; 514/948

[58] Field of Search .......... 424/439, 440, 424/441; 514/948

[56] References Cited

U.S. PATENT DOCUMENTS

| | | | |
|---|---|---|---|
| 122,507 | 1/1872 | Wills | 514/948 |
| 3,114,642 | 12/1963 | Meisel | 99/134 |
| 3,438,787 | 4/1969 | Du Ross | 99/134 |
| 3,738,845 | 6/1973 | Liebrand | 99/134 R |
| 4,225,627 | 9/1980 | Moore | 426/548 |
| 4,241,092 | 12/1980 | Halik | 426/96 |
| 4,311,722 | 1/1982 | Vink et al. | 424/440 |
| 4,335,147 | 6/1982 | Sollich | 426/295 |
| 4,389,393 | 6/1983 | Schor et al. | 424/441 |
| 4,452,825 | 6/1984 | Klaik et al. | 424/440 |
| 4,515,769 | 5/1985 | Merritt et al. | 424/440 |
| 4,695,463 | 9/1987 | Yang | 424/440 |
| 4,749,575 | 6/1988 | Rotman | 424/440 |
| 4,764,378 | 8/1988 | Keith | 424/435 |
| 4,885,173 | 12/1989 | Stanley et al. | 424/440 |

OTHER PUBLICATIONS

"Sustained Release Dosage Forms", *The Theory and Practice of Industrial Pharmacy*, pp. 450–456.

Klech, Cathy M., et al., "Temperature Dependence of Non–Fickian Water Transport and Swelling in Glassy Gelatin Matrices", *Pharmaceutical Research*, vol. 6, No. 7, 1989, pp. 564–570.

Thomas, Alan, et al., "Technologists Update Sugar Substitutes Status", *Candy Industry*, Mar. 1989, pp. 80–85.

*Primary Examiner*—Raj Bawa

*Attorney, Agent, or Firm*—Workman, Nydegger & Seeley

[57] ABSTRACT

Compositions and methods of manufacture for producing a medicament composition capable of absorption through the mucosal tissues of the mouth, pharynx, and esophagus. The present invention relates to such compositions and methods which are useful in administering lipophilic and nonlipophilic drugs in a dose-to-effect manner such that sufficient drug is administered to produce precisely a desired effect. The invention also relates to a manufacturing technique that enables a therapeutic agent or drug to be incorporated into a flavored dissolvable matrix. An appliance or holder is preferably attached to the dissolvable matrix. Employing the present invention the drug may be introduced into the patient's bloodstream almost as fast as through injection, and much faster than using the oral administration route, while avoiding the negative aspects of both of these methods. The present invention achieves these advantages by incorporating the drug into a carbohydrate, fat, protein, wax, or other dissolvable matrix composition. The dissolvable matrix may include permeation enhancers to increase the drug absorption by the mucosal tissues of the mouth. The matrix composition may also include pH buffering agents to modify the salival pH thereby increasing the absorption of the drug through the mucosal tissues.

198 Claims, 2 Drawing Sheets

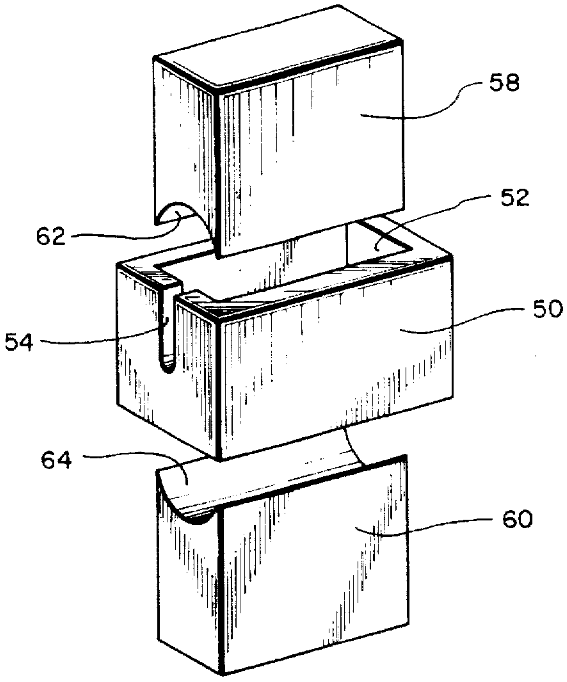
FIG. 6
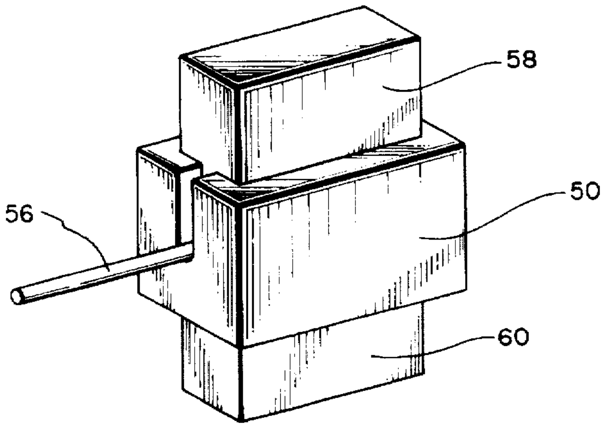
FIG. 7
FIG. 8
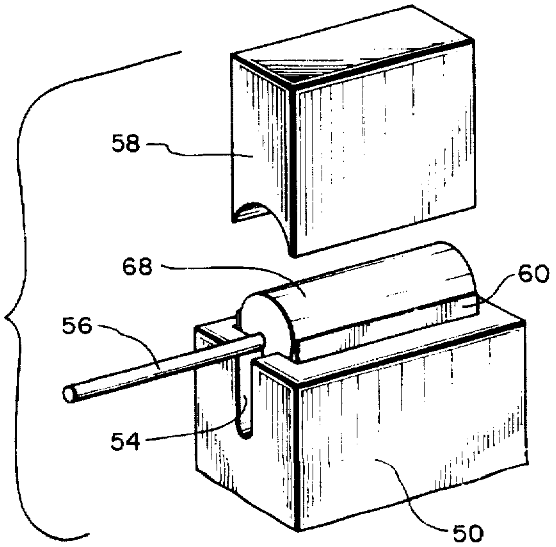

COMPOSITIONS AND METHODS OF MANUFACTURING OF ORAL DISSOLVABLE MEDICAMENTS

RELATED APPLICATIONS

This application is a continuation application of application Ser. No. 08/333.233 filed Nov. 2, 1994, (now abandoned) which is a continuation of Ser. No. 08/152.396, filed on Nov. 12, 1993 (now abandoned), which is a divisional of Ser. No. 07/403.751, filed Sep. 5, 1989, U.S. Pat. No. 5,288,497, which is a continuation-in-part of Ser. No. 07/060.045, filed Jun. 8, 1987, U.S. Pat. No. 4,863,737, which is a continuation-in-part of Ser. No. 06/729,301, filed May 1, 1985, U.S. Pat. No. 4,671,953. For purposes of disclosure, each of the above identified patents are incorporated herein by specific reference.

BACKGROUND

1. The Field of the Invention

The present invention relates to compositions and methods of manufacture of oral dissolvable matrixes for medicaments used in the buccal, sublingual, pharyngeal, and esophageal transmucosal delivery of the medicaments. More particularly, the present invention is directed to compositions, and methods and apparatus for producing such compositions, for noninvasive administration of dose-to-effect amounts of medicaments through the mucosal tissues of the mouth, pharynx, and esophagus.

2. The Background of the Invention

Recently, numerous advancements have taken place in the field of pharmacology and pharmaceutics with respect to the administration of drugs to treat various conditions. Despite the tremendous advancements in the field, however, drugs continue to be administered using substantially the same techniques that have been used for many decades. The vast majority of pharmaceutical agents continue to be administered either orally or by injection. Nevertheless, it is frequently found in the art that neither of these administration routes are effective in all cases, and both administration routes suffer from several disadvantages.

Oral administration is probably the most prevalent method of administering pharmacological medicaments. The medicament is generally incorporated into a tablet, capsule, or a liquid base, and then swallowed. The oral administration modality is often preferred because of its convenience. In addition, oral administration is generally nonthreatening, painless, and simple to accomplish for most patients.

Nevertheless, oral administration of drugs suffers from several disadvantages. One disadvantage is that pediatric and geriatric patients frequently have difficulty swallowing pills and other solid dosage-forms, and such patients often refuse to cooperate in swallowing a liquid medication. In addition, for many medicaments, the act of swallowing the medicament often requires fluids and increases gastric volume and the likelihood of nausea and vomiting.

A further problem with oral administration is that the rate of absorption of the drug into the bloodstream after swallowing varies from patient to patient. The absorption of the drug is dependent upon the movement of the drug from the stomach to the small and large intestines and the effects of secretions from these organs and on the resulting pH within the stomach and intestines. Anxiety and stress can dramatically reduce these movements and secretions, prevent or reduce the final effects of the drug, and delay onset of the drug's effects.

Most significant is the fact that there is normally a substantial delay between the time of oral administration and the time that the therapeutic effect of the drug begins. As mentioned above, the drug must pass through the gastrointestinal system in order to enter the bloodstream; this typically takes forty-five minutes or longer. As mentioned above, anxiety and stress often increase this delay.

For many applications, such as premedication before surgery or where immediate relief from pain or a serious medical condition or immediate effectiveness of the drug is required, this delay is unacceptable. In modern outpatient units and operating rooms where rapid turnover of patients is essential for cost containment, extensive delays in the action of a drug are simply unacceptable.

An additional disadvantage of oral administration is that many drugs almost immediately experience metabolism or inactivation. The veins from the stomach and the small and large intestines pass directly through the liver. Thus, drugs entering the bloodstream must first pass through the liver before distribution into the general blood circulation. More than sixty percent of most drugs (and essentially one hundred percent of certain drugs) are removed from the patient's bloodstream during this "first pass" through the liver. The result is that oral administration is impractical for many drugs, particularly many central nervous system and many cardiovascular-acting drugs that are used for rapid onset in critical care situations, as a premedication prior to surgery, or for the induction of anesthesia.

Further, additional stress is placed on the liver as it removes the excess drug from the bloodstream. This is particularly severe if the drug treatment has been occurring over an extended period of time. The liver may become overloaded with the drug's metabolite which then must be excreted. As a result, there is an increased risk of hepatic or renal disorders.

Another difficulty encountered in administering drugs orally is that dosages are prepared or determined for use with an "average" patient. Most drugs have widely varying effects on different patients. These effects depend upon patient habits, subtle genetic differences between patients, blood volumes, age, and numerous other known and unknown factors. Introducing a bolus of drug orally does not provide the ability to control the precise dose needed to obtain the desired effect, rather the dose is estimated in order to produce an average effect in an average patient. The result may be underdosing or overdosing a particular patient.

Underdosing a patient because of a low susceptibility to the drug fails to evoke the response sought by the physician. Overdosing the patient can result in dangerous depression of vital body functions, especially the heart and lungs. This can cause prolonged respiratory depression (necessitating mechanical ventilation after surgery), cardiac depression, and cardiac arrest.

In order to avoid some of the disadvantages of oral administration, injection is frequently used. Injecting a drug (generally intravenously or intramuscularly), results in rapid entry of the drug into the patient's bloodstream. In addition, this type of delivery avoids the removal of large quantities of the drug by the patient's liver. As a result, less total drug is usually needed compared to orally administered drugs. The drug instead becomes rapidly distributed to various portions of the patient's body before exposure to the liver.

Most patients, particularly children and geriatric adults, have an aversion to injections. In some patients, this aversion may be so pronounced as to make the use of injections a serious concern. Since intense psychological stress can exacerbate a patient's debilitated condition, it sometimes becomes undesirable to use injections where the patient is seriously ill or suffers from a debilitating condition or injury.

In addition, individual variations in susceptibility in the metabolism of various drugs (particularly drugs with central nervous system activity) are even more profound when utilizing the injection route. In many instances to prevent overdosing, it is the practice to inject a patient with a lower than average dose and then supplement the dose with additional injections as necessary. This "titration" makes necessary the use of repeated injections, which in turn greatly increases stress on the patient. Again, a precise dose cannot be administered to produce a precise effect because the patient's response varies widely depending on the specific characteristics of the specific patient.

One common approach to preparing a patient for surgery is to orally administer a sedative or anxiolytic. Although quick onset of sedation or anxiolysis has not always been a critical factor, it is more so now. Changing practices, including the increased use of outpatient units for day surgery and the pressures for cost containment in modern medicine, dictate rapid onset of action and the use of an absolutely ideal dose in order to avoid increased costs of caring for patients with delayed recovery secondary to slightly overdosing with anesthesia. Effective oral administration of premedication drugs with central nervous system activity (which cause a rapid onset of sedation and anxiolysis without producing excessive sedation) is often difficult to accomplish.

Some investigators have suggested that it may be possible to administer medication through the buccal mucosa of the cheek pouch or by sublingual administration. See, U.S. Pat. No. 4,671,953 entitled "METHODS AND COMPOSITIONS FOR NONINVASIVE ADMINISTRATION OF SEDATIVES, ANALGESICS, AND ANESTHETICS." Such administration through the mucosal tissues of the mouth, pharynx, and esophagus of therapeutic drugs possesses a distinct usefulness. Administration of drugs by this route does not expose the drug to the gastric and intestinal digestive juices. In addition, the drugs largely bypass the liver on the first pass through the body, thereby avoiding additional metabolism and/or inactivation of the drug.

Generally the drugs which are administered by any of the methods described above have an unpleasant taste. As a result, in order to allow for buccal or sublingual administration through the oral mucosal tissues, it is also necessary to incorporate the drug into some type of pleasant tasting mass, such as a "candy" matrix.

In the manufacture of medicated candy products by existing methods, the therapeutic agent is added to a molten candy mass. The resultant mixture is then thoroughly mixed to ensure proper distribution of the drug within the molten candy mass. The mixture is then poured into a mold cavity while still molten and allowed to solidify into a solid mass. Alternatively, the hot candy mass may be poured into molds, the size and shape of which may be determined as desired.

For effective application of the drug, the final candy product may contain the drug uniformly distributed throughout in order to ensure uniform levels of medication. Alternatively, for some applications, varying concentrations within known and controlled ranges may be desired to vary the rate of drug administration. Difficulties are encountered in attempting to blend solid drugs in a uniform or otherwise carefully controlled manner. Many drugs are insoluble, or only partially soluble, in one or more of the ingredients of the hard candy base. Thus, the resultant product is often found to be lacking in uniform or controlled distribution of the drug.

In addition, it is often found that when the temperature of the candy mass is increased in order to enable a more uniform distribution (generally to a temperature above approximately 230° C.), considerable decomposition of the drug takes place. While the extent of decomposition may vary, high temperatures are generally undesirable in the handling and processing of medications. Thus, the process of formation of the candy product may itself degrade and/or inactivate the therapeutic agent.

Furthermore, many presently available medicated candy lozenges tend to crumble when placed in the mouth. As a result, uniform release of the drug into the mucosal tissues does not take place. Rather, the crumbled lozenge is mostly chewed, and swallowed, and the drug enters the bloodstream through the stomach and intestines as described above. Thus, it will be appreciated that candy lozenges have very definite limitations for use in the administration of a drug through the oral mucosal tissues. As a result, lozenges have not been used to administer potent, fast-acting drugs, such as drugs that affect the central nervous system, the cardiovascular system, or the renal vascular system.

While the administration of certain drugs through the oral mucosal tissues has shown promise, development of a fully acceptable method for producing a medication in a desirable form and administering the medication has been elusive. It has not been possible to develop an acceptable candy product for use with most drugs without heating the product to the point where degradation will be expected.

It should also be noted that pH conditions within the mouth may tend to adversely affect the administration of certain lipophilic drugs by the mucosal administration route. It has been found in the art that administration of drugs through the mucosal tissues generally occurs best when the drug is in the unionized form. Variations in pH affect the percentage of the drug which is unionized at a particular point in time. As a result, the pH conditions within the mouth can limit the effectiveness of certain drugs administered buccally or sublingually in that those conditions cause the drug to exist in the ionized form which is largely unavailable for transfer across the mucosal tissues.

Other potent drugs are substantially nonlipophilic and do not naturally permeate mucosal tissues. Hence it would be a significant advancement in the art of administering potent, fast-acting drugs, if suitable methods and compositions permitted both lipophilic and nonlipophilic drugs to be administered transmucosally.

It would be another important advancement in the art of administering potent, fast-acting drugs, if suitable methods and compositions provided a precise dosage to a precise effect in every patient. A related advancement in the art would be to provide such methods and compositions that avoid the disadvantages of overdosing, underdosing, and the immediate metabolism encountered in the "first pass effect," yet do not involve injection by needle into the patient.

It would be a further significant advancement in the art to provide methods and compositions for incorporating drugs (including insoluble drugs) into a soluble matrix without heating the mixture to the point that degradation occurs. It would be a related advancement in the art to provide such a method which provided the capability of uniformly incorporating insoluble drugs into the soluble matrix.

Such compositions and methods of manufacture are disclosed and claimed herein.

BRIEF SUMMARY AND OBJECTS OF THE INVENTION

The present invention relates to compositions and methods of manufacture for producing medicament compositions for use in administering potent, fast-acting drugs transmucosally. Furthermore, the present invention relates to such compositions and methods which are useful in administering drugs in a dose-to-effect manner such that sufficient drug is administered to produce precisely the desired effect. The invention also relates to a manufacturing technique that enables both lipophilic and nonlipophilic therapeutic agents to be incorporated into a flavored dissolvable matrix material and to attach the matrix mixture onto an appliance or holder. In use, the present invention provides for the administration of drugs through the mucosal tissue of the mouth, pharynx, and esophagus, thereby avoiding the problems of both injection and oral administration.

Employing the present invention, the drug may be introduced into the patient's bloodstream almost as fast as through injection, and much faster than using the oral administration route, while avoiding the negative aspects of both methods. A dosage-form within the scope of the present invention can be used to administer drugs in a dose-to-effect manner, or until the precise desired effect is achieved.

The present invention achieves these advantages by incorporating the drug into a dissolvable matrix material. The dissolvable matrix may include carbohydrates, fats, proteins, waxes (natural and synthetic), hydrocarbons, and other materials which safely dissolve in the mouth. The dissolvable matrix, or dosage-form, can be used to administer drugs in a dose-to-effect manner, or until the precise desired effect is achieved. The dosage-form preferably has an appliance or handle attached thereto to permit removal from the patient's mouth.

The manufacturing methods of the present invention overcome many of the limitations previously encountered in forming a medicated lozenge. The present invention teaches the combination of ingredients by geometric dilution. That is, the two smallest ingredients by weight are first thoroughly mixed, then the next smallest ingredient or ingredients by weight equal to the weight of the previous ingredients is added and is thoroughly mixed with the existing mixture. This procedure is repeated until all of the components, including the desired therapeutic agents, are fully combined.

After mixing, the mixture may be compressed, poured into a mold cavity, dehydrated, freeze dried, or otherwise formed as an integral drug delivery system. In some embodiments within the scope of the present invention, specific confectionery components are combined in order for the mixture to form an integral solid mass. These components may include, for example, compressible confectioner's sugar, sorbitol, mannitol, and maltodextrin.

In other embodiments within the scope of the present invention, certain fats, waxes, or hydrocarbons may be combined with the desired therapeutic agent and compressed to form a dissolvable drug delivery system. Sugars and other carbohydrates, flavors, dyes, mold releasing agents, binding agents, and flavor modifiers may also be combined with the dissolvable matrix material and therapeutic agent before being compressed.

In yet other embodiments within the scope of the present invention, therapeutic agents may be combined with hydrogels or gelatins to form a dissolvable drug delivery system.

These embodiments overcome many of the problems of the prior art. According to the present invention, insoluble drugs can be added to the matrix without the necessity of attempting to dissolve the drug. In addition, the high temperatures, which are generally required to form a molten candy matrix of the prior art and which can cause degradation of some drugs, are avoided using the present invention. Therefore, even drugs with relatively low melting points or those drugs which can experience decomposition below their melting points, can be incorporated into a dissolvable dosage-form.

A further advantage of the present invention is that flavoring problems are overcome in many cases. Flexibility in adding flavors is provided in that solubility of the components is not required in order to incorporate any particular flavor into the matrix. Thus, flavorings, drugs, and other components (which may be insoluble in liquid form) are easily mixed when they exist as a dry powder.

Buffering agents and other types of pH control can also be added simultaneously in order to provide for maximum drug efficiency. It will be appreciated that drugs in the unionized form are more readily transported across the mucosal membrane. Therefore, if pH conditions can be adjusted to maximize the percentage of unionized drug available, the effectiveness of the drug is maximized.

Buffering agents are particularly important for those drugs that partially ionize within the pH range of the mouth, such as weak acid and weak base drugs. Generally, buffering agents are more important when hydrophilic drugs are used because those drugs usually have lower mucosal permeability and dissolve more readily in saliva within the mouth.

Permeation enhancers may also be incorporated within the dissolvable matrix to improve the permeability of the mucosal membrane. The permeability of both lipophilic and nonlipophilic drugs may be improved by using suitable permeation enhancers.

Various dosage-form configurations are also possible employing the present invention. For example, layers of drug may be interspersed between layers of a dissolvable composition. Since the present invention teaches the use of different dissolvable matrix materials which can be compressed, poured, dried, or otherwise formed into a solid dosage-form, virtually any desired type of mold can be used for the formation of the dosage-form.

It may also be desirable to incorporate a handle or holder in the dissolvable matrix material as the matrix is being formed. Alternatively, the handle may be glued to the matrix material by a dissolvable bonding agent, such as confectioner's glue, once the dissolvable matrix is formed. The handle provides for easy removal of the dissolvable matrix from the mouth of the patient once the desired effect has been achieved. This is a substantial improvement over existing methods of administering drugs through the mucosal tissues of the mouth.

The present invention also provides the advantage of controlling the dissolution rate of the composition once it is administered to a patient. This can be accomplished in a number of ways. First, the dissolution rate may be modified chemically by including a hydrophobic agent (such as calcium stearate) to slow dissolution or lactose to enhance dissolution. The solubility of the selected matrix material, e.g., gelatin, fat, protein, wax, etc., likewise affects the dissolution rate. Dissolution may also be controlled by the extent to which the mixture is mechanically compressed. In addition, dissolution can be accomplished by varying the vigor with which the patient sucks on the dissolvable matrix.

A drug administered through the oral mucosal tissues from a dissolvable matrix within the scope of the present invention will quickly enter the patient's bloodstream through the veins which serve these tissues. Appropriate monitoring of the patient's reaction to the drugs which have an observable or monitorable effect (such as a drug affecting the central nervous, cardiovascular, or renal vascular systems) will indicate when the drug has evoked a suitable response. The dosage-form may then be removed, or its rate of consumption may be modified in order to maintain the desired effect.

It will be appreciated that the ever present risk of overdosing a patient is substantially minimized through the use of the present invention. According to the present invention, the drug dose is given over a period of time rather than all at once, and the administration rate can be adjusted if it appears to be necessary. Once a sufficient drug response has been achieved, the patient can simply stop sucking on the dosage-form or the patient or medical professional can easily remove the dosage-form from the patient's mouth.

It is, therefore, a primary object of the present invention to provide methods of manufacture and compositions in order to accomplish the noninvasive administration of a drug to a patient in order to rapidly induce a desired systemic effect.

It is another object of the present invention to provide methods of manufacture for forming a drug-containing dissolvable matrix, which methods avoid degradation of the drug, overcome problems related to insolubility of the various components in the dissolvable matrix, and provide a product which is not likely to crumble in the patient's mouth.

Yet another object of the present invention is to provide compositions and methods for the transmucosal administration of both lipophilic and nonlipophilic drugs. A related object of the present invention is the use of suitable permeation enhancers which improve drug permeation across the mucosal membrane.

It is another object of the present invention to provide compositions which allow for precise control of the dosage and effect of the drug to be administered.

These and other objects and features of the present invention will become more fully apparent from the following description and appended claims taken in conjunction with the accompanying drawings.

BRIEF DESCRIPTION OF THE DRAWINGS

FIG. 6 is a perspective view of mold for forming a dissolvable drug matrix which uses horizontal compression.

FIG. 7 is a perspective view of the mold shown in FIG. 6 in the process of forming a dosage-form within the scope of the present invention.

FIG. 8 is a perspective view of the mold shown in FIG. 6 with the bottom die pushing a completed dosage-form out of the mold.

DETAILED DESCRIPTION OF THE PREFERRED EMBODIMENTS

1. General Discussion

Figure 1:
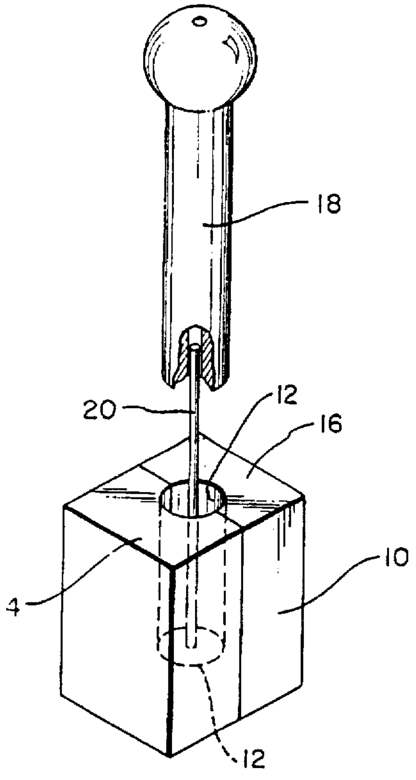
FIG. 1 is a perspective view of a mold for forming the dissolvable drug matrix along with an associated ram.

The present invention is related to methods of manufacture and compositions which facilitate the transmucosal delivery of a medication. Simply stated, the present invention relates to a dosage-form, or similar type of composition, which contains a therapeutic drug. The drug is delivered to the patient through the mucosal tissues of the mouth, pharynx, and esophagus as the patient sucks on the drug-containing dosage-form.

This particular method of delivery overcomes several of the limitations encountered in the delivery of drugs either orally or by injection. One of the primary advantages of the present invention is the ability to introduce drugs to a patient in a "dose-to-effect" manner. The drug is given to the patient until the precisely desired effect is obtained; this is in distinction to prior art methods where a predetermined quantity of the drug is introduced to the patient. Once the desired effect is obtained, the patient or the medical professional simply removes the dosage-form from the patient's mouth.

The present invention discloses a method of producing a dosage-form containing one or more therapeutic agents. The present invention overcomes many of the problems encountered generally in incorporating drugs into a dissolvable matrix. For example, the present invention teaches the mixing of solid powders or liquids at room temperature, as opposed to liquid components at elevated temperatures. The degradation of drugs, which often occurs at the elevated temperatures needed to produce a molten candy mass, is thereby avoided. This facilitates use of drugs having relatively low melting points, or those drugs which can experience decomposition below their melting points. The mixing can also be done at very low temperatures. In this way, evaporation of any volatile ingredients is minimized and the "stickiness" of sticky ingredients is reduced making them more crumbly.

In addition, because solid powders or liquids are combined together, constituents which may be chemically incompatible when in a heated solution or suspension can be mixed. In forming medicated confections by known methods, severe problems are encountered in that the medication, flavorings, and other components may be insoluble when placed in the same liquid environment. In addition, problems of chemical incompatibility between ingredients is eliminated in the present invention.

Once the desired constituents are thoroughly mixed, they may be formed into a solid dosage-form. In other cases the constituents are wetted to form a slurry, dried, and then compressed (sometimes referred to as "slugging"). In one embodiment, the ingredients are compressed to form the dosage-form. Typically, compressive forces in the range from approximately 2,000 Newtons to approximately 5,000 Newtons are preferred. As a result, the compressed powdered matrix is held together by physical means rather than by chemical means. The extent of the compressive forces can be modified to vary the rate that the dosage-form will dissolve in a patient's mouth. The greater the compressive forces that form the mixture, the slower the dissolution of the matrix material in the mouth.

In other embodiments within the scope of the present invention, the desired constituents are formed into the dosage-form by dehydration, freeze drying (lyophilization), pouring into a mold, spraying onto a suitable holder, vapor deposition, or other known techniques in the art.

According to the present invention, the dissolvable matrix composition is attached to a holder or handle. Attaching the dissolvable matrix to a holder facilitates the administering of precise dosages. Once a particular effect is induced, the dosage-form can be withdrawn using the holder as described above.

The attachment of the dissolvable matrix material to a holder may be made by incorporating the holder into the dissolvable matrix as the dosage-form is being formed. Alternatively, the holder may be glued, compressed, screwed, snapped, or otherwise attached to the dissolvable matrix once the matrix is formed. A dosage-form may be assembled immediately prior to use by sliding disks of drug and dissolvable matrix onto an appropriately configured holder. Also, the dissolvable matrix may be sprayed or otherwise deposited onto a handle during formation. In addition, the dissolvable matrix may be formed around an insert onto which a holder can be attached.

It will be appreciated that compression or attachment of the drug-containing matrix onto a holder can facilitate the transmucosal absorption of a variety of therapeutic agents. Attachment to a holder also facilitates verifiable transfer of the medication to the patient. The holder provides a convenient point of reference concerning quantities of drug administered at any particular point in time; it is easy to determine how much of the dosage-form has been dissolved in the patient's mouth.

Localization of effects by some therapeutic agents such as local anesthetic agents, antiplaque agents, local antipruritic agents, local antisecretory agents, and local antifungal agents can also be accomplished according to the present invention. Immediate systemic effects from central nervous system-acting drugs (such as sedation, anxiolysis, analgesia, amnesia, and anesthesia), cardiovascular-acting agents (such as antihypertensives and antianginal drugs), renal vascular-acting agents, and numerous other therapeutic agents can also be accomplished by employing the present invention.

Placing a drug dosage onto a holder also facilitates the temporary removal of medication for inspection or the reduction of the effect when necessary. Unlike administration of drugs orally or even sublingually, the present composition can easily be removed to assess the effect induced at any particular time. When a pill or lozenge is used, removal from the patient's mouth at an intermediate stage to assess effect is generally impractical, if not impossible.

Dissolvable matrixes attached to a holder can also avoid aspiration of the confection. One major problem with existing lozenges and the like is their tendency to crumble. Once the lozenge crumbles, controlled transmucosal delivery is less ideal.

The present invention provides the capability of providing a good tasting medication. With many drugs, it has previously been extremely difficult to provide a good tasting medicine because of the extreme bitterness or other unpleasant taste of many drugs. Using the present invention, favorable taste characteristics can be accomplished by adding various flavors, sweeteners, and the like to form an ideal mix of products. Since the components are combined as solids or liquids (or even liquids that are slowly released from microsponges), problems associated with combining flavoring components insoluble in a molten candy mass are avoided.

It is important to note that it is possible, according to the present invention, to use the free acid form or the free base form of certain drugs and to buffer those drugs such that extremes in pH, and resulting bad taste, are avoided.

Another important feature of the present invention is the incorporation of permeation enhancers within the dissolvable matrix. The permeation enhancers improve the mucosal membrane permeability to lipophilic and nonlipophilic drugs. Thus, the compositions and methods within the scope of the present invention permit the use of lipophilic as well as nonlipophilic drugs.

2. Methods of Manufacture

In order to prepare a desirable drug-containing dissolvable matrix for formation into a dosage-form, it is generally necessary to combine several general types of components. These components include the types of components used to prepare typical confections, the desired drug, and other chemically active ingredients such as buffering agents, permeation enhancers, and the like. The types of components involved generally fall into the following categories:

(1) flavorings,
(2) sweeteners,
(3) flavor enhancers,
(4) releasing agents,
(5) buffers,
(6) one or more therapeutic agents,
(7) dissolvable matrix material, and
(8) permeation enhancers.

The components may be a releasable or slowly releasable liquid.

As mentioned above, it is preferred that these components each be provided in a form which facilitates mixing, such as a dry powder. This provides for convenient combination of the ingredients, even if they happen to be insoluble or otherwise chemically incompatible. All the incipients or inactive ingredients should be on the GRAS list ("generally regarded as safe").

A wide range of flavors are available for preparing good tasting and desirable medications within the scope of the present invention. These are required in order to mask the unpleasant taste of the drug. Flavorings may be combined, as desired, to produce a particular flavor mix which is compatible with a particular medication. Some of the confectioner's flavorings which have been used in the context of the present invention include artificial vanilla, vanilla cream, mint, cherry, spearmint, grape, coconut, chocolate, menthol, licorice, lemon, and butterscotch.

Each of these flavorings is obtainable in a concentrated powder form. Other flavorings known in the confectionery arts may also be acceptable because of the ease of combining the ingredients of the present invention. Any number of flavorings may be combined in any desired ratio in order to produce the specific desired taste characteristics required for any particular application. For example, flavor combinations may be varied in order to be compatible with the flavor characteristics of any specific drug.

In order to produce a desirable color for the end product, artificial colorings may also be added to the composition. The flavorings described above are generally a white powder, as are the other major components. Therefore, additional coloring is necessary if a colored end product is desired. Coloring may also be important as a code to indicate the type and concentration of drug contained within a particular dissolvable matrix. Any type of color known to be "FD&C" certified may be used to provide coloring to the product.

In order to provide a good tasting medication, it is necessary to add sweeteners to the composition. Sweeteners which are presently preferred include aspartame (NutraSweet®) and compressible confectioner's sugar. Other sweeteners, such as fructose, sorbitol, mannitol, xylitol, cyclamates, acesulfame K, thaumatin, sucralose, alitame, PS99/PS100, glycyrrhizin, monellin, stevioside, miraculin, or L-sugars may also be acceptable for use within the scope of the present invention. Again, it is desired that a sweetener or combination of sweeteners be obtained which is compatible with the drug and the other components such that a good tasting confection is produced.

Maltodextrin and cyclodextran may also be added to provide a better tasting composition. Maltodextrin and cyclodextran are generally employed in order to dissipate unpleasant flavors (such as the bitter taste of most drugs) within the composition. In addition, maltodextrin is a highly compressible powder which facilitates the formation of compressible dosage-forms within the scope of the present invention.

For some applications, it may be desirable to add a flavor enhancer to the composition in order to achieve a good tasting product. Flavor enhancers provide a more pleasant sensation in the patient's mouth during consumption of the dosage-form. Flavor enhancers within the scope of the present invention include materials such as ribotide (a nucleotide) and monosodium glutamate ("msg").

In certain medications, it may also be desirable to add a lubricating agent in order to release the dosage-form from the mold. Such agents may also provide a certain amount of waterproofing. As mentioned above, the rate of dissolution of the dosage-form within the patient's mouth may be controlled chemically, as well as physically, through the extent of compression of the composition. These lubricating or releasing agents may include substances such as compritol 888 (glyceryl behenate), calcium stearate, and sodium stearate. These agents may enhance dissolution or they may inhibit dissolution as necessary.

Lubricating agents are also useful in those embodiments wherein a powder mixture is funneled into a chute during manufacture. Lubricating agents and surfactants improve product flow and avoid static electricity charge buildup within the formulation which may cause the ingredients to separate due to electrostatic forces.

As will be discussed in more detail below, it may also be desirable to include buffering agents within the composition. Buffering agents provide the ability to place the medication in the mouth in a favorable pH environment for passage across the mucosal tissues of the mouth, pharynx, and esophagus. Buffering agents incorporated within the composition can be used to effect a pH change in the salival environment of the mouth in order to favor the existence of a unionized form of the active ingredient or drug which more readily moves through the mucosal tissues.

In addition, appropriate pH adjustment can aid in producing a more palatable product with drugs which are either severely acidic (and thus sour) or severely basic (and thus bitter). As a result, a buffer system such as citric acid/sodium citrate has been found to be desirable for addition into the dissolvable matrix. A phosphate buffer system may also be used.

A suitable permeation enhancer capable of improving the drug permeability across the mucosal membrane may also be included in the dissolvable composition. Permeation enhancers are particularly important when nonlipophilic drugs are used, but may be valuable for lipophilic drugs as well. Examples of typical permeation enhancers which may be used within the scope of the present invention are discussed below.

It will be appreciated that miscellaneous other agents such as lactose, to provide filling and bulk, may also be desirable. Other filling and bulking agents of the type known in the art may also be used. Gelatin may be used to provide filling and bulking agents in other embodiments of the present invention.

Added to the dissolvable matrix described above will be the appropriate therapeutic agent or drug. As will be discussed in more detail below, various types of drugs are easily incorporated into the matrix compositions of the present invention. These include agents which affect the central nervous system, the cardiovascular system, or the renal vascular system.

A typical dosage-form within the scope of the present invention may include the following general ingredients: flavoring, sweetener, flavor enhancer, releasing agent, buffer, therapeutic agent(s), and/or bulk dissolvable matrix. The "bulk dissolvable matrix" may include hydrogel-, gelatin-, fat-, protein-, wax-based, and other similar dissolvable substances. Appropriate changes in flavoring ingredients can be made to mask or optimize flavor perception in order to achieve ultimate acceptance of the dosage-form by the desired patient group, be it adult, juvenile, pediatric, or neonate.

Each of the components is mixed with the other components to produce the compositions of the present invention. It is presently preferred to use the method of geometric dilution in mixing the various components. Using this method, the two smallest ingredients by weight (as a proportion of the final product) are first mixed together thoroughly.

When complete mixing has been obtained between those two components, the next smallest ingredient or ingredients by weight equal to the weight of the previous ingredients is added and mixed thoroughly with the existing mixture. This procedure is repeated until all of the components are added to the mix and mixed thoroughly with all other components.

Geometric dilution provides for complete and thorough mixing of all of the components. Using the method described above, there is little chance for incomplete mixing and uneven distribution of components throughout the mix. It will be recognized that this is an advancement over the art in that existing methods may result in incomplete mixing because of the insolubility of the products.

Once complete mixing is accomplished, the mixture is formed into a solid dissolvable matrix composition. In one embodiment, the mixture is compressed under relatively high forces to provide a coherent dosage. Compressive forces in the range of from approximately 2,000 Newtons to approximately 5,000 Newtons are presently preferred, however, any force which is sufficient to compress the ingredients into a coherent, integrated mass could be used.

In other embodiments within the scope of the present invention, the desired constituents are formed into the dosage-form by dehydration, freeze drying (lyophilization), pouring into a mold, spraying onto a suitable holder, vapor deposition, or other known techniques in the art.

When employing the present invention, there is no need to heat the mixture to a molten mass as has been the practice in the past in forming drug-containing confections. As a result, heat degradation of the drug component is avoided while good mixing and a uniform product are provided.

The dissolvable matrix may be attached to a holder such as a handle or other similar type of holder. The holder may be glued to the matrix by dissolvable adhesive such as confectioner's glue, liquid sorbitol, or wax. Alternatively, the holder may be compressed or molded into the dissolvable matrix as described above.

The figures illustrate several methods of forming the dosage-form, as well as methods of attaching the holder to the dosage-form. FIG. 1 discloses a mold block 10. The interior of mold block 10 includes a cavity 12 formed in any desired shape so that the ingredients described above can be compressed or molded to form an appropriately shaped dosage. Mold block 10 may comprise two separate halves 14 and 16. Each half of the mold block 10 can be removed in order to remove the dosage-form once it is formed.

Also illustrated in FIG. 1 is ram 18. Ram 18 is configured so that it fits into the cavity 12 and compresses the dosage-form into the base of cavity 12. Ram 18 may have a hole disposed through its interior in order to accommodate handle 20. Thus, handle 20 can be placed into the mass of dosage-form prior to compression. Ram 18 will then compress the dosage-form tightly around handle 20. Following compression of the dosage-form, the handle is securely bound in place.

Figure 2:
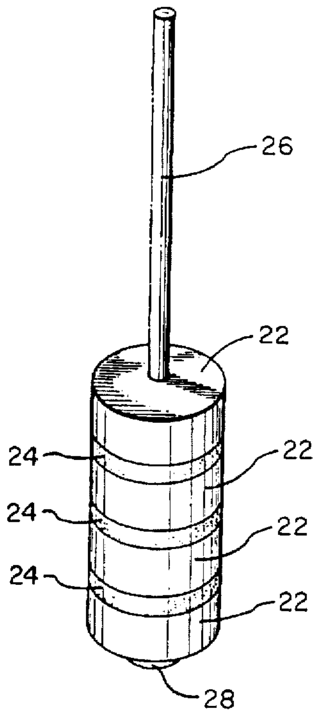
FIG. 2 is a perspective view of one embodiment of a dosage-form within the scope of the present invention.

FIG. 2 discloses an additional embodiment of the dosage-form of the present invention. The dosage-form illustrated in FIG. 2 has alternating layers of dissolvable matrix 22 and a drug matrix 24. Each alternating segment is disk-shaped with the width of the disk being varied according to particular needs. Disks 22 and 24 easily slide over handle 26 and seat against button 28. Thus, the method of assembly of the dosage-form can be adapted to produce various dosages to fit varying circumstances. Indeed, the patient himself may be capable of assembling an appropriate dosage-form and varying the content of the medicament to correspond to his specific needs at any particular time.

Figure 3:
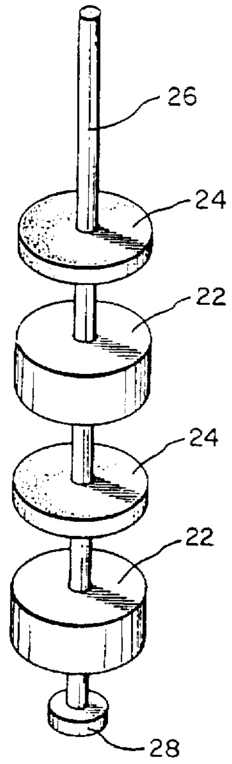
FIG. 3 is an exploded plan view of the embodiment of the dosage-form shown in FIG. 2.

FIG. 3 illustrates the method of assembling the embodiment of the invention as illustrated in FIG. 2. In FIG. 3, the drug matrix 24 and dissolvable matrix 22 are spaced apart along handle 26. As can be appreciated from FIG. 3, disks 22 and 24 will slide onto handle 26 and will seat against button 28. The number of disks and the composition of these disks can be easily varied to meet particular patient needs. Various concentrations of a drug, or even multiple drugs, may be administered in this manner.

Handle 26 may take various shapes. For example, it may be desirable for handle 26 to be oval or triangular in cross section. This would prevent disks 24 and 26 from turning on the handle. In addition, an additional sleeve (not shown) may be positioned over the exposed portion of the handle with a catch that engages handle 26 so that disks 24 and 26 are locked in place.

Figure 4:
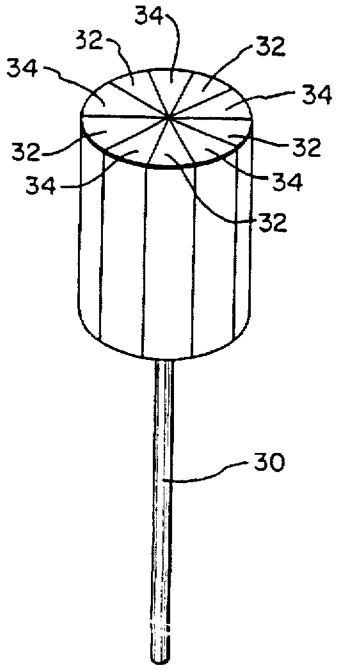
FIG. 4 is a perspective view of an alternative embodiment of the dosage-form of the present invention.

FIG. 4 illustrates a further embodiment of a dosage-form within the scope of the present invention. In FIG. 4, the drug and dissolvable matrix are divided laterally along the cylindrical mass of the dosage-form. Thus, pie-shaped segments of drug 32 and dissolvable matrix material 34 are pressed together around handle 30. As illustrated in FIG. 4, drug segments 32 and dissolvable segments 34 may alternate around a periphery of the dosage-form. Alternatively, the spacing of the segments may be varied to provide other appropriate levels of drug dosage.

Figure 5:
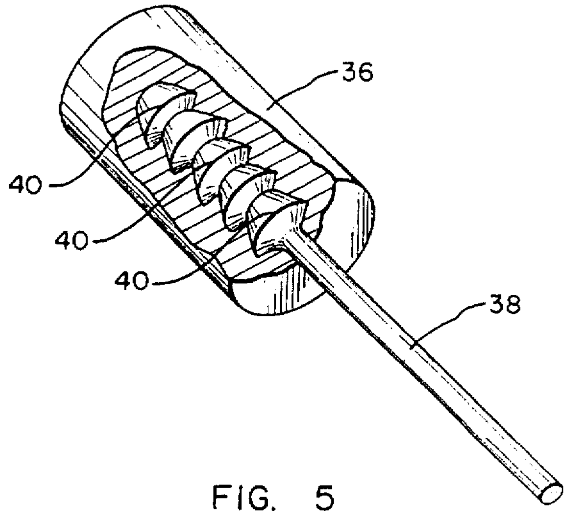
FIG. 5 is a cutaway plan view of an alternative embodiment of a dosage-form of the present invention illustrating one method of attachment of the handle to the dissolvable matrix.

FIG. 5 illustrates an alternate method of attachment between the dosage-form 36 and the handle 38. Handle 38 illustrated in FIG. 5 is constructed with a plurality of protrusions 40. Protrusions 40 extend toward the exposed portion of the handle such that they prevent the dosage-form from sliding off the handle. Thus, when the dosage-form 36 is compressed around handle 38, the dosage-form is securely bound to the handle.

FIGS. 6–8 illustrate a mold block 50 for forming a dosage-form within the scope of the present invention. Mold block 50 defines a die cavity 52. A slot 54, located on one edge of mold block 50 facilitates insertion and removal of holder 56. A top die 58 and a bottom die 60 are configured to be inserted within die cavity 52. The top and bottom die both have concave surfaces 62 and 64, respectively.

To prepare a dosage-form using mold block 50, a quantity of dissolvable matrix material which contains the medicament is placed in die cavity 52 on concave surface 64. A holder 56 is positioned within slot 54 such that a portion of the holder is within the die cavity. An additional amount of dissolvable matrix material is placed in the die cavity on top of the holder. The top and bottom dies then compress the dissolvable matrix material around the holder thereby preparing a dosage-form 68. In order to remove the dosage-form from the mold block, the bottom die pushes the completed dosage-form out of the die cavity as shown in FIG. 8.

It can be seen, therefore, that the present invention provides a great deal of flexibility in the construction of an appropriate drug-containing confection. The quantity of drug contained in any confection can be varied within wide ranges. In addition, various methods of attachment of the confection to the handle are available in order to provide a wide range of flexibility.

3. Control of pH in View of Drug pKa

It is well known that most drugs are weak acids or weak bases and are present in solution in both the unionized and ionized forms. It has been found that the unionized portion of the drug is usually lipid soluble and can readily diffuse across the cell membrane. The ionized portion, conversely, is often lipid insoluble and in some instances, may not effectively penetrate the lipid membrane of the cell. As a result, drugs in the ionized form are generally inefficient in producing a drug effect on the central nervous, cardiovascular, and renal vascular systems.

Whether a drug exists in the ionized or unionized form is largely dependent upon its pKa, and correspondingly on the pH of the solution. The present invention provides the unique ability to control the pH of the solution and thus the ratio of unionized to ionized form of the drug.

Ingredients of the dissolvable matrix or other dosage-form can be designed to impart sufficient change in the pH of the saliva within the mouth such that the concentration of the unionized drug is increased. When the percentage of unionized drug is increased, transmucosal absorption of the drug is correspondingly increased. Therefore, by influencing the salival pH environment, it is possible to greatly improve the extent and rapidity of actual drug absorption, and therefore, the initial onset of the effect of the drug. Adding pH buffering systems (such as phosphate or citrate buffer systems) into the dosage-form can greatly facilitate delivery of the drug in the unionized (lipid soluble) form.

It is often desirable for the pKa to range from approximately 5 to approximately 8 in order to maximize drug delivery. pKa is defined as the negative logarithm (base 10) of the dissociation constant (Ka). pKa may also be defined as the pH at which a given acid is 50% ionized and 50% unionized. The term pKb is used when referring to a base. pKa and pKb can be calculated from pH, if the concentrations of the charged and uncharged species are known, using the well-known Henderson-Hasselbach equation if concentrations of the charged and uncharged species are known. The Henderson-Hasselbach equation is as follows:

$$pKb = pH + \log\left|\frac{\text{charged}}{\text{uncharged}}\right| \text{ for bases}$$

$$pKa = pH + \log\left|\frac{\text{uncharged}}{\text{charged}}\right| \text{ for acids}$$

From these equations, the unionized portion of the drug will be increased by lowering the pH for weak acid drugs and increasing the pH for weak base drugs.

The effect on the pKa of varying pH, and thus on the unionized drug available, is extremely dramatic. For example, sodium methohexital (the salt of a weak acid), a potent central nervous system-acting drug, has a pKa of 7.9. If at the same time the general pH of the saliva is about 7.5, these values can then be placed in the Henderson-Hasselbach equation as follows:

$$7.9 = 7.5 + \log (X)$$

where X is the ratio of the unionized to the ionized drug form. Solving this calculation indicates that under typical conditions in the mouth, 72% of the methohexital available would exist in the unionized form. As was mentioned above, the unionized drug form is the primary form that is transported across the lipid cell membrane.

In the event that the salival pH is buffered down to approximately 6.7, the ratio of unionized to ionized drug changes dramatically. This results in a corresponding dramatic change in the amount of drug available. Under these conditions, 94% of the drug available exists in the unionized form.

Comparing the ratio of unionized to ionized drug produced under the two sets of pH conditions described above, it can be seen that dramatic changes occur. Changing the pH from 7.5 to 6.7 produces a substantial improvement in the concentration of unionized drug available for delivery across the lipid membrane. This results directly in a dramatic improvement in drug delivery across the cell membranes in the mouth and a corresponding increase in the effectiveness of the drug administered.

Changes in pH such as those discussed above can be accomplished by incorporating particular buffer systems within the confection composition. One presently preferred buffer system is a citric acid/sodium citrate system; however, other conventional buffers (such as phosphate) may also be used. By using such a buffer, dramatically better results may be achieved such that buccal drug absorption is a fully feasible and optimal delivery method.

It will be appreciated that an additional advantage of the change of the pH may be that the taste characteristics of the drug can be improved. Drugs which are very high in pH typically are very bitter in taste. As the pH drops, the taste becomes less bitter, then salty, and may eventually become sour. Flavorings can more adequately improve the taste characteristics of drugs in the lower pH ranges. As a result, in addition to improving the drug delivery, buffering pH may also improve the taste characteristics of the composition.

Although the foregoing discussion has focused on the alteration of pH to enhance drug permeability by increasing the percentage of unionized drug forms, pH may enhance drug permeability by unknown mechanisms. For example, pH may affect drug molecular configuration which enhances drug permeability. Nonetheless, drug pH is often an important consideration in drug administration.

4. Mucosal Membrane Permeation Enhancers

As discussed above, most drugs are present in solution in both the unionized and ionized forms. Generally only lipid soluble or lipophilic drugs readily diffuse across mucosal membranes. However, it has been found that nonlipophilic drugs may diffuse across mucosal membranes if the mucosal membrane is treated with a permeation enhancer. It has also been found that certain permeability enhancers can significantly enhance the permeability of lipophilic and nonlipophilic drugs.

Typical permeation enhancers may include bile salts such as sodium cholate, sodium glycocholate, sodium glycodeoxycholate, taurodeoxycholate, sodium deoxycholate, sodium lithocholate chenocholate, chenodeoxycholate, ursocholate, ursodeoxycholate, hydrodeoxycholate, dehydrocholate, glycochenocholate, taurochenocholate, and taurochenodeoxycholate. Other permeation enhancers such as sodium dodecyl sulfate ("SDS"), dimethyl sulfoxide ("DMSO"), sodium lauryl sulfate, salts and other derivatives of saturated and unsaturated fatty acids, surfactants, bile salt analogs, derivatives of bile salts, or such synthetic permeation enhancers as described in U.S. Pat. No. 4,746,508 may also be used.

It is almost impossible to predict which enhancer will work best for a given drug. For each individual drug, only experiments can tell which enhancer is the most suitable. However, it is generally believed that bile salts are good enhancers for hydrophilic drugs and long chain fatty acids, their salts, derivatives, and anologs are more suitable for lipophilic drugs. DMSO, SDS, and medium chain fatty acids (C-8 to about C-14) their salts, derivatives, and anologs may work for both hydrophilic and lipophilic drugs.

The effectiveness of some enhancers may vary depending on the chemical compound to be permeated. One particular enhancer may work very well on one drug but may not have any effect on another drug. For example, oleic acid greatly improves the transdermal permeability of estradiol, a very lipophilic drug, but oleic acid does not have any effect on the transmucosal permeability of glucose, a very hydrophilic drug. Although it is possible to speculate whether a given enhancer may or may not enhance a given drug's permeability, the actual effectiveness of an enhancer should be verified experimentally.

The permeation enhancer concentration within the dissolvable matrix material may be varied depending on the potency of the enhancer and rate of dissolution of the dissolvable matrix. Other criteria for determining the enhancer concentration include the potency of the drug and the desired lag time. The upper limit for enhancer concentration is set by toxic effect to or irritation limits of the mucosal membrane.

The following is a list of typical enhancers and an exemplary concentration range for each enhancer:

| Enhancer | Operational Concentration | Preferred Range |
|---|---|---|
| sodium cholate | 0.02%–50% | 0.1%–16% |
| sodium dodecyl sulfate | 0.02%–50% | 0.1%–2% |
| sodium deoxycholate | 0.02%–50% | 0.1%–16% |
| taurodeoxycholate | 0.02% - solubility | 0.1%–16% |
| sodium glycocholate | 0.02% - solubility | 0.1%–16% |
| sodium taurocholate | 0.02% - solubility | 0.1%–16% |
| DMSO | 0.02% - solubility | 5%–50% |

5. Suitable Therapeutic Agents

In order for the present invention to operate effectively, it is necessary that the therapeutic agent incorporated within the dissolvable matrix be capable of permeating the mucosal membrane either alone or by suitable adjustments in the environmental pH, or other chemical modification or in combination with a suitable permeation enhancer. In some embodiments, the therapeutic agent may be microencapsulated or incorporated into microsponges.

The present invention has applicability to a variety of drugs affecting the central nervous system. For example, the present invention may easily be utilized in the administration of opioid agonists (such as fentanyl, alfentanil, sufentanil, lofentanil, and carfentanil), opioid antagonists (such as naloxone and nalbuphene), butyrophenones (such as droperidol and haloperidol); benzodiazepines (such as valium, midazolam, triazolam, oxazolam, and lorazepam); GABA stimulators (such as etomidate); barbiturates (such as Thiopental, methohexital, thiamazol, pentobarbital, and hexabarbital); diisopropylphenols drugs (such as diprivan); and other central nervous system-acting drugs such as levodopa. It will be appreciated that other drugs may also be utilized within the scope of the present invention either singly or in combination.

Table 1 lists some of the CNS-acting drugs which are suitable for incorporation into the dosage-form of the present invention, as well as some of the characteristics of those drugs.

TABLE 1

| GENERIC DRUG | DRUG CLASS | DOSE RANGE |
|---|---|---|
| methohexital | barbiturate | 10–500 mg |
| pentobarbital | barbiturate | 50–200 mg |
| thiamylal | barbiturate | 10–500 mg |
| thiopental | barbiturate | 50–500 mg |
| fentanyl | opioid agonist | 0.05–5 mg |
| alfentanil | opioid agonist | 0.5–50 mg |
| sufentanil | opioid agonist | 5–500 μg |
| lofentanil | opioid agonist | 0.1–100 μg |
| carfentanil | opioid agonist | 0.2–100 μg |
| naloxone | opioid antagonist | 0.05–5 mg |
| nalbuphene | opioid antagonist | 1–50 mg |
| diazepam | benzodiazepine | 1–40 mg |
| lorazepam | benzodiazepine | 1–4 mg |
| midazolam | benzodiazepine | 0.5–25 mg |
| oxazepam | benzodiazepine | 5–40 mg |
| triazolam | benzodiazepine | 250–1000 mg |
| droperidol | buterophenone | 1–20 mg |
| haloperidol | buterophenone | 0.5–10 mg |
| propanidid | eugenol | 1–10 mg |
| etomidate | GABA stimulator | 5–60 mg |
| propofol | substituted phenol | 3–50 mg |
| ketamine | phencyclidine | 5–300 mg |
| diprivan | substituted phenol | 5–20 mg |

Drugs having effects on the cardiovascular and renal vascular systems may also be administered using a dosage-form of the present invention. A few examples of such drugs are identified in Table 2.

TABLE 2

| GENERIC DRUG | DRUG CLASS | DOSE RANGE |
|---|---|---|
| Bretylium | antiarrhythmic | 50–500 mg |
| Captopril | ACE inhibitor | 25–75 mg |
| Clonidine | antihypertensive | 0.1–0.5 mg |
| Dopamine | renal vascular | 0.5–5 mg |
| Enalapril | ACE inhibitor | 5–15 mg |
| Esmolol | antihypertensive/angina | 100–250 mg |
| Furosemide | diuretic | 20–100 mg |
| Isosorbide | angina | 2.5–40 mg |
| Labetolol | antihypertensive | 100–400 mg |
| Lidocaine | antiarrhythmic | 50–250 mg |
| Metolazone | diuretic | 5–50 mg |
| Metoprolol | antihypertensive | 25–100 mg |
| Nadolol | antihypertensive | 40–160 mg |
| Nifedipine | antihypertensive/ angina/vasodilator | 10–40 mg |
| Nitroglycerin | antihypertensive/angina | 0.4–1.0 mg |
| Nitroprusside | hypotensive | 10–50 mg |
| Propranolol | antihypertensive/angina | 0.1–50 mg |

In addition to the foregoing, there are many other drugs which can be administered using a dosage-form of the present invention. Exemplary of such drugs are those identified in Table 3.

TABLE 3

| GENERIC DRUG | DRUG CLASS | DOSE RANGE |
|---|---|---|
| Benzquinamide | antiemetic | 25–100 mg |
| Meclizine | antiemetic | 25–100 mg |
| Metoclopramide | antiemetic | 5–20 mg |
| Prochlorperazine | antiemetic | 5–25 mg |
| Trimethobenzamide | antiemetic | 100–2500 mg |
| Clotrimazole | antifungal | 10–20 mg |
| Nystatin | antifungal | 100,000–500,000 units |

TABLE 3-continued

| GENERIC DRUG | DRUG CLASS | DOSE RANGE |
|---|---|---|
| Carbidopa | antiparkinson | with levodopa 10–50 mg |
| Levodopa | antiparkinson | 100–750 mg |
| Sucralfate | antisecretory | 1–2 grams |
| Albuterol | bronchodilator | 0.8–1.6 mg |
| Aminophylline | bronchodilator | 100–500 mg |
| Beclomethasone | bronchodilator | 20–50 μg |
| Dyphylline | bronchodilator | 100–400 mg |
| Epinephrine | bronchodilator | 200–500 μg |
| Flunisolide | bronchodilator | 25–50 μg |
| Isoetharine | bronchodilator | 170–680 μg |
| Isoproterenol HCl | bronchodilator | 60–260 μg |
| Metaproterenol | bronchodilator | 0.65–10 mg |
| Oxtriphylline | bronchodilator | 50–400 mg |
| Terbutaline | bronchodilator | 2.5–10 mg |
| Theophylline | bronchodilator | 50–400 mg |
| Ergotamine | antimigraine | 2–4 mg |
| Methysergide | antimigraine | 2–4 mg |
| Propranolol | antimigraine | 80–160 mg |
| Suloctidil | antimigraine | 200–300 mg |
| Ergonovine | oxytocic | 0.2–0.6 mg |
| Oxytocin | oxytocic | 5–20 units |
| Desmopressin acetate | antidiuretic | 10–50 μg |
| Lypressin | antidiuretic | 7–14 μg |
| Vasopressin | antidiuretic | 2.5–60 units |
| Insulin | antihyperglycemic | 1–100 units |

In addition to the foregoing drugs, certain macromolecular drugs (such as β-endorphin, enkephalins, bradykinin, aniotensin I, gonadotropic hormones, adrenocorticotropic hormone (ACTH), calcitonin, parathyroid hormone, and growth hormone), polysaccharides (such as heparin), antigens, antibodies, and enzymes may be adapted for transmucosal administration within the scope of the present invention.

When incorporating a drug into a dissolvable matrix within the scope of the present invention, the amount of drug used will generally differ from the amount used in more traditional injection and oral administration techniques. Depending upon the lipophilic nature of the drug, its potency, the use of permeation enhancers, and the drug's end use, the total concentration of the drug in the typical dosage-form may contain up to 50 times more than the amount of drug which would typically be used in an injection, but it may also contain significantly less than the amount used orally, and it may also contain less than the amount used in some intramuscular injections. For purposes of example, Tables 1, 2, and 3 set forth presently contemplated ranges of the dosages of certain drugs which could be typically used.

A wide variety of drugs may be used within the scope of the present invention. The present invention allows drugs to be incorporated within the dissolvable matrix which would otherwise be insoluble, unpleasant tasting, or have other undesirable characteristics. This capability is provided by the various formation techniques of the dosage-form. The present invention also allows both lipophilic as well as nonlipophilic drugs to be utilized depending on the use of permeation enhancers.

As was mentioned above, methohexital is one presently preferred drug for use in the dissolvable dosage-form of the present invention. Tests were run in which methohexital dosage-forms were given to six volunteers. The dosage-forms each contained 500 milligrams of methohexital. Each patient experienced the sedative effects of the drug in a matter of minutes after beginning to suck on the dosage-form. These tests indicated that the dosage-form of the present invention is effective in administering methohexital in a dose-to-effect manner.

Using the methohexital dosage-form described above, it was possible to produce either mild or heavy sedation or induce anesthesia. By removing the dosage-form when the ideal degree of sedation was achieved, it was possible to gradually increase sedation to the desired level.

In addition, the results show that the use of oral transmucosal methohexital significantly decreases the drug dosage required to produce optimal sedation when compared to rectal administration. The dosage was reduced from between 25 and 30 mg/kg when methohexital is administered rectally to between 6 and 8 mg/kg methohexital is given by way of the oral transmucosal dosage-form. The use of an enhancer may reduce this dosage even more.

In summary, it will be appreciated that a wide variety of drugs can be used within the scope of the present invention. At the same time, several benefits are provided. Efficient delivery of the drug is facilitated while at the same time drug degradation is avoided. The drug can also be administered in a dose-to-effect manner so that the drug effect produced is precisely controlled.

5. Examples of the Present Invention

The following examples are given to illustrate various embodiments which have been made or may be made in accordance with the present invention. These examples are given by way of example only, and it is to be understood that the following examples are not comprehensive or exhaustive of the many types of embodiments of the present invention which can be prepared in accordance with the present invention.

EXAMPLE 1

In this example, methohexital was incorporated into a dissolvable matrix form. Methohexital is a known potent lipophilic drug useful as an anxiolytic, sedative and for anesthetizing a patient. Its high potency and lipophilicity makes it an excellent drug for transmucosal administration in accordance with the present invention.

A suitable mixture was prepared by combining the following ingredients as follows:

| Ingredient | % | grams |
|---|---|---|
| citric acid | 1% | 0.2 |
| ribotide | 2% | 0.4 |
| compritol 888 | 2% | 0.4 |
| aspartame | 2% | 0.4 |
| vanilla microcaps | 5% | 1.0 |
| vanilla cream microcaps | 5% | 1.0 |
| wild cherry microcaps | 3% | 0.6 |
| peppermint microcaps | 3% | 0.6 |
| compressible sugar | 20% | 4.0 |
| methohexital sodium | 25% | 5.0 |
| maltodextrin | 32% | 6.4 |
| | 100% | 20 |

The ingredients were combined in a mixer in such a fashion as to ensure a uniform distribution of all ingredients within the mixture. Aliquots of 2 grams each were then hydraulically compressed around a commercially available wax-coated compressed paper holder, using a force sufficient to provide a final volume of 2 cubic centimeters. The procedure resulted in the preparation of 10 oral transmucosal dosage-forms, each containing 0.5 grams of methohexital.

EXAMPLE 2

In this example, methohexital was incorporated into a dissolvable matrix form. Gelatin was selected as the dissolvable matrix material. Methohexital is a known potent lipophilic drug useful as an anxiolytic, sedative and for anesthetizing a patient. Its high potency and lipophilicity makes it an excellent drug for transmucosal administration in accordance with the present invention.

A suitable mixture was prepared by combining the following ingredients as follows:

| Ingredient | % | grams |
|---|---|---|
| citric acid | 1% | 0.2 |
| ribotide | 2% | 0.4 |
| compritol 888 | 2% | 0.4 |
| aspartame | 2% | 0.4 |
| vanilla microcaps | 5% | 1.0 |
| vanilla cream microcaps | 5% | 1.0 |
| wild cherry microcaps | 3% | 0.6 |
| peppermint microcaps | 3% | 0.6 |
| methohexital sodium | 25% | 5.0 |
| gelatin | 52% | 10.4 |
| | 100% | 20 |

The ingredients were combined in a mixer in such a fashion as to ensure a uniform distribution of all ingredients within the mixture. Aliquots of 2 grams each were then formed by dehydration. The procedure resulted in the preparation of 10 oral transmucosal dosage-forms, each containing 0.5 grams of methohexital.

It will be appreciated that similar dosage-forms may be produced using other dissolvable matrix materials such as fats, waxes (natural or synthetic), proteins, hydrogels, dissolvable resins, or other suitable dissolvable matrix materials.

6. Summary

In summary, it can be seen that the present invention accomplishes the objects set forth above. The present invention provides compositions and methods of manufacture for administering a drug in a precise dose in order to obtain a rapid effect. In addition, the present invention provides methods for forming a drug containing dissolvable matrix having the following attributes:

(1) drugs having relatively low melting points can be used without degrading the drug;

(2) drugs that are volatile can be incorporated into the matrix;

(3) disagreeable flavor characteristics can be masked;

(4) insoluble ingredients can be used;

(5) chemically incompatible ingredients can be used;

(6) buffer forming reagents can be added to optimize the ratio of ionized and nonionized drug form;

(7) chemical agents can be added to modify the dissolution characteristics of the drug;

(8) permeation enhancers can be added to increase the drug absorption;

(9) lipid soluble mixtures can be added to increase drug absorption;

(10) dissolution characteristics can be modified mechanically by changing the compressive forces used to form the dissolvable matrix;

(11) stratification of active ingredients can be accomplished;

(12) the dosage can be modified by utilizing an assembly of dosage units onto a holder; and

(13) both lipophilic and nonlipophilic drugs can be suitably used.

The present invention, therefore, provides the ability to provide precise control over the dosage and effect of the drug. This is obtained by transmucosal administration of the drug by sucking a drug-containing dissolvable dosage-form having a handle. As a result, the precise dosage and effect can be obtained.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A solid drug-containing dosage-from for use in the transmucosal oral and sublingual delivery of the drug to a patient, said solid dosage-form consisting essentially of:

a soluble matrix selected from the group consisting of a carbohydrate, wax, fat, protein, or mixture thereof;

buffers dispersed throughout the soluble matrix;

a pharmacologically effective dose of a drug being capable of absorption through mucosal tissues of the mouth, pharynx, and esophagus and being dispersed throughout the matrix and formed into a solid integral mass which is capable of being sucked on while held within the mouth to dissolve the integral mass in the mouth of the patient to release the drug for absorption through mucosal tissues of the mouth, pharynx, and esophagus during the period of holding within the mouth resulting in dissolution of the integral mass in the mouth of the patient; and attached holder means secured to the integral mass so as to form a drug-containing dosage-form, the holder means being configured to permit convenient insertion and removal of the drug-containing integral mass into and out of the mouth of the patient and to permit administration of the dosage form in a dose-to-effect manner.

2. A drug-containing dosage-form for use in transmucosal delivery of the drug to a patient as defined in claim 1, wherein the soluble matrix further includes a water-insoluble component dispersed throughout the matrix in order to slow the dissolution of the matrix in the mouth of the patient.

3. A drug-containing dosage-form for use in transmucosal delivery of the drug to a patient as defined in claim 1, wherein the drug is lipophilic.

4. A drug-containing dosage-form for use in transmucosal delivery of the drug to a patient as defined in claim 1, wherein the drug is nonlipophilic.

5. A drug-containing dosage-form as recited in claim 1, wherein the drug is a central nervous system-acting drug.

6. A drug-containing dosage-form as recited in claim 1, wherein the drug is dispersed uniformally throughout the matrix.

7. A drug-containing dosage-form as recited in claim 1, wherein the drug is methohexital.

8. A drug-containing dosage-form as recited in claim 1, wherein the drug is pentobarbital.

9. A drug-containing dosage-form as recited in claim 1, wherein the drug thiamylal.

10. A drug-containing dosage-form as recited in claim 1, wherein the drug is thiopental.

11. A drug-containing dosage-form as recited in claim 1, wherein the drug is hexabarbital.

12. A drug-containing dosage-form as recited in claim 1, wherein the drug is fentanyl.

13. A drug-containing dosage-form as recited in claim 1, wherein the drug is alfentanil.

14. A drug-containing dosage-form as recited in claim 1, wherein the drug is sufentanil.

15. A drug-containing dosage-form as recited in claim 1, wherein the drug is lofentanil.

16. A drug-containing dosage-form as recited in claim 1, wherein the drug is carfentanil.

17. A drug-containing dosage-form as recited in claim 1, wherein the drug is naloxone.

18. A drug-containing dosage-form as recited in claim 1, wherein the drug is nalbuphine.

19. A drug-containing dosage-form as recited in claim 1, wherein the drug is diazepam.

20. A drug-containing dosage-form as recited in claim 1, wherein the drug is lorazepam.

21. A drug-containing dosage-form as recited in claim 1, wherein the drug is lormetazepam.

22. A drug-containing dosage-form as recited in claim 1, wherein the drug is midazolam.

23. A drug-containing dosage-form as recited in claim 1, wherein the drug is oxazepam.

24. A drug-containing dosage-form as recited in claim 1, wherein the drug is triazolam.

25. A drug-containing dosage-form as recited in claim 1, wherein the drug is droperidol.

26. A drug-containing dosage-form as recited in claim 1, wherein the drug is haloperidol.

27. A drug-containing dosage-form as recited in claim 1, wherein the drug is propanidid.

28. A drug-containing dosage-form as recited in claim 1, wherein the drug is etomidate.

29. A drug-containing dosage-form as recited in claim 1, wherein the drug is propofol.

30. A drug-containing dosage-form as recited in claim 1, wherein the drug is ketamine.

31. A drug-containing dosage-form as recited in claim 1, wherein the drug is levodopa.

32. A drug-containing dosage-form as recited in claim 1, wherein the drug is bretylium.

33. A drug-containing dosage-form as recited in claim 1, wherein the drug is captopril.

34. A drug-containing dosage-form as recited in claim 1, wherein the drug is clonidine.

35. A drug-containing dosage-form as recited in claim 1, wherein the drug is dopamine.

36. A drug-containing dosage-form as recited in claim 1, wherein the drug is enalapril.

37. A drug-containing dosage-form as recited in claim 1, wherein the drug is esmolol.

38. A drug-containing dosage-form as recited in claim 1, wherein the drug is furosemide.

39. A drug-containing dosage-form as recited in claim 1, wherein the drug is isosorbide.

40. A drug-containing dosage-form as recited in claim 1, wherein the drug is labetalol.

41. A drug-containing dosage-form as recited in claim 1, wherein the drug is lidocaine.

42. A drug-containing dosage-form as recited in claim 1, wherein the drug is metolazone.

43. A drug-containing dosage-form as recited in claim 1, wherein the drug is metoprolol.

44. A drug-containing dosage-form as recited in claim 1, wherein the drug is nadolol.

45. A drug-containing dosage-form as recited in claim 1, wherein the drug is nifedipine.

46. A drug-containing dosage-form as recited in claim 1, wherein the drug is nitroglycerin.

47. A drug-containing dosage-form as recited in claim 1, wherein the drug is nitroprusside.

48. A drug-containing dosage-form as recited in claim 1, wherein the drug is propranolol.

49. A drug-containing dosage-form as recited in claim 1, wherein the drug is benzquinamide.

50. A drug-containing dosage-form as recited in claim 1, wherein the drug is meclizine.

51. A drug-containing dosage-form as recited in claim 1, wherein the drug is metoclopramide.

52. A drug-containing dosage-form as recited in claim 1, wherein the drug is prochlorperazine.

53. A drug-containing dosage-form as recited in claim 1, wherein the drug is trimethobenzamide.

54. A drug-containing dosage-form as recited in claim 1, wherein the drug is clotrimazole.

55. A drug-containing dosage-form as recited in claim 1, wherein the drug is nystatin.

56. A drug-containing dosage-form as recited in claim 1, wherein the drug is carbidopa.

57. A drug-containing dosage-form as recited in claim 1, wherein the drug is sucralfate.

58. A drug-containing dosage-form as recited in claim 1, wherein the drug is albuterol.

59. A drug-containing dosage-form as recited in claim 1, wherein the drug is aminophylline.

60. A drug-containing dosage-form as recited in claim 1, wherein the drug is beclomethasone.

61. A drug-containing dosage-form as recited in claim 1, wherein the drug is dyphylline.

62. A drug-containing dosage-form as recited in claim 1, wherein the drug is epinephrine.

63. A drug-containing dosage-form as recited in claim 1, wherein the drug is flunisolide.

64. A drug-containing dosage-form as recited in claim 1, wherein the drug is isoetharine.

65. A drug-containing dosage-form as recited in claim 1, wherein the drug is isoproterenol HCL.

66. A drug-containing dosage-form as recited in claim 1, wherein the drug is metaproterenol.

67. A drug-containing dosage-form as recited in claim 1, wherein the drug is oxtriphylline.

68. A drug-containing dosage-form as recited in claim 1, wherein the drug is terbutaline.

69. A drug-containing dosage-form as recited in claim 1, wherein the drug is theophylline.

70. A drug-containing dosage-form as recited in claim 1, wherein the drug is ergotamine.

71. A drug-containing dosage-form as recited in claim 1, wherein the drug is dihydroergotamine.

72. A drug-containing dosage-form as recited in claim 1, wherein the drug is methysergide.

73. A drug-containing dosage-form as recited in claim 1, wherein the drug is suloctidil.

74. A drug-containing dosage-form as recited in claim 1, wherein the drug is ergonovine.

75. A drug-containing dosage-form as recited in claim 1, wherein the drug is oxytocin.

76. A drug-containing dosage-form as recited in claim 1, wherein the drug is desmopressin acetate.

77. A drug-containing dosage-form as recited in claim 1, wherein the drug is lypressin.

78. A drug-containing dosage-form as recited in claim 1, wherein the drug is vasopressin.

79. A drug-containing dosage-form as recited in claim 1, wherein the drug is insulin.

80. A drug-containing dosage-form as recited in claim 1, wherein the drug is a B-endorphin.

81. A drug-containing dosage-form as recited in claim 1, wherein the drug is an enkephalin.

82. A drug-containing dosage-form as recited in claim 1, wherein the drug is a bradykinin.

83. A drug-containing dosage-form as recited in claim 1, wherein the drug is angiotensin I.

84. A drug-containing dosage-form as recited in claim 1, wherein the drug is a gonadotropic hormone.

85. A drug-containing dosage-form as recited in claim 1, wherein the drug is an adrenocorticotropic hormone.

86. A drug-containing dosage-form as recited in claim 1, wherein the drug is calcitonin.

87. A drug-containing dosage-form as recited in claim 1, wherein the drug is a parathyroid hormone.

88. A drug-containing dosage-form as recited in claim 1, wherein the drug is a growth hormone.

89. A drug-containing dosage-form as recited in claim 1, wherein the drug is heparin.

90. A drug-containing dosage-form as recited in claim 1, wherein the drug is a barbiturate.

91. A drug-containing dosage-form as recited in claim 1, wherein the drug is an opioid agonist.

92. A drug-containing dosage-form as recited in claim 1, wherein the drug is an opioid antagonist.

93. A drug-containing dosage-form as recited in claim 1, wherein the drug is a benzodiazepine.

94. A drug-containing dosage-form as recited in claim 1, wherein the drug is a butyrophenone.

95. A drug-containing dosage-form as recited in claim 1, wherein the drug is a GABA stimulator.

96. A drug-containing dosage-form as recited in claim 1, wherein the drug is a substituted phenol.

97. A drug-containing dosage-form as recited in claim 1, wherein the drug is a phencyclidine.

98. A drug-containing dosage-form as recited in claim 1, wherein the drug is an antiarrhythmic.

99. A drug-containing dosage-form as recited in claim 1, wherein the drug is a beta blocker.

100. A drug-containing dosage-form as recited in claim 1, wherein the drug is an ACE inhibitor.

101. A drug-containing dosage-form as recited in claim 1, wherein the drug is a calcium channel blocker.

102. A drug-containing dosage-form as recited in claim 1, wherein the drug is an antihypertensive.

103. A drug-containing dosage-form as recited in claim 1, wherein the drug is an antihypertensive/anti-anginal.

104. A drug-containing dosage-form as recited in claim 1, wherein the drug is a diuretic.

105. A drug-containing dosage-form as recited in claim 1, wherein the drug is anti-anginal.

106. A drug-containing dosage-form as recited in claim 1, wherein the drug is antihypertensive/anti-anginal/vasodilator-acting.

107. A drug-containing dosage-form as recited in claim 1, wherein the drug is a hypotensive-acting.

108. A drug-containing dosage-form as recited in claim 1, wherein the drug is an antiemetic.

109. A drug-containing dosage-form as recited in claim 1, wherein the drug is an antifungal.

110. A drug-containing dosage-form as recited in claim 1, wherein the drug is an antiparkinson.

111. A drug-containing dosage-form as recited in claim 1, wherein the drug is a bronchodilator.

112. A drug-containing dosage-form as recited in claim 1, wherein the drug is an antimigraine.

113. A drug-containing dosage-form as recited in claim 1, wherein the drug is an oxytocic.

114. A drug-containing dosage-form as recited in claim 1, wherein the drug is an antidiuretic.

115. A drug-containing dosage-form as recited in claim 1, wherein the drug is an antihyperglycemic.

116. A drug-containing dosage-form as recited in claim 1, wherein the drug is a macromolecular.

117. A drug-containing dosage-form as recited in claim 1, wherein the drug is an amino acid.

118. A drug-containing dosage-form as recited in claim 1, wherein the drug is a polysaccharide.

119. A drug-containing dosage-form as recited in claim 1, wherein the drug is a polypeptide.

120. A drug-containing dosage-form as recited in claim 1, wherein the drug is an antigen.

121. A drug-containing dosage-form as recited in claim 1, wherein the drug is a nucleoside.

122. A drug-containing dosage-form as recited in claim 1, wherein the drug is an antibody.

123. A drug-containing dosage-form as recited in claim 1, wherein the drug is a vitamin.

124. A drug-containing dosage-form as recited in claim 1, wherein the drug is an enzyme.

125. A drug-containing dosage-form as recited in claim 1, wherein the drug is central nervous system-acting.

126. A drug-containing dosage-form as recited in claim 1, wherein the drug is cardiovascular-acting.

127. A drug-containing dosage-form as recited in claim 1, wherein the drug is renal vascular-acting.

128. A drug-containing dosage-form as recited in claim 1, wherein the drug is a sedative.

129. A drug-containing dosage-form as recited in claim 1, wherein the drug is anxiolytic.

130. A drug-containing dosage-form as recited in claim 1, wherein the drug is analgesic.

131. A drug-containing dosage-form as recited in claim 1, wherein the drug is an amnestic.

132. A drug-containing dosage-form as recited in claim 1, wherein the drug is an anesthetic.

133. A drug-containing dosage-form as recited in claim 1, wherein the drug is a local anesthetic agent.

134. A drug-containing dosage-form as recited in claim 1, wherein the drug is an antiplaque agent.

135. A drug-containing dosage-form as recited in claim 1, wherein the drug is a local antipruritic agent.

136. A drug-containing dosage-form as recited in claim 1, wherein the drug is a local antisecretory agent.

137. A drug-containing dosage-form as recited in claim 1, wherein the drug is a local antifungal agent.

138. A drug-containing dosage-form as recited in claim 1, wherein the drug is an antibiotic.

139. A drug-containing dosage-form as recited in claim 1, wherein the drug is nicotine.

140. A drug-containing dosage-form as recited in claim 1, wherein the drug is atropine.

141. A drug-containing dosage-form as recited in claim 1, wherein the drug is scopolamine.

142. A drug-containing dosage-form as recited in claim 1, wherein the drug is ondansetron.

143. A drug-containing dosage-form as recited in claim 1, wherein the drug is sumatriptan.

144. A drug-containing dosage-form as recited in claim 1, wherein the drug is ketorolac tromethamine.

145. A drug-containing dosage-form as recited in claim 1, wherein the drug is meclofenamate.

146. A drug-containing dosage-form as recited in claim 1, wherein the drug is piroxicam.

147. A drug-containing dosage-form as recited in claim 1, wherein the drug is ketoprofen.

148. A drug-containing dosage-form as recited in claim 1, wherein the drug is indomethacin.

149. A drug-containing dosage-form as recited in claim 1, wherein the drug is ibuprofen.

150. A drug-containing dosage-form as recited in claim 1, wherein the drug is diclofenac.

151. A drug-containing dosage-form as recited in claim 1, wherein the drug is flurbiprofen.

152. A drug-containing dosage-form as recited in claim 1, wherein the drug comprises a permeation enhancer.

153. A drug-containing dosage-form as recited in claim 1, wherein the drug is sodium cholate.

154. A drug-containing dosage-form as recited in claim 1, wherein the drug is sodium dodecyl sulfate.

155. A drug-containing dosage-form as recited in claim 1, wherein the drug is sodium deoxycholate.

156. A drug-containing dosage-form as recited in claim 1, wherein the drug is taurodeoxycholate.

157. A drug-containing dosage-form as recited in claim 1, wherein the drug is sodium glycocholate.

158. A drug-containing dosage-form as recited in claim 1, wherein the drug is sodium taurocholate.

159. A drug-containing dosage-form as recited in claim 1, wherein the drug is dimethyl sulfoxide.

160. A drug-containing dosage-form as recited in claim 1, wherein the drug is sodium glycodeoxycholate.

161. A drug-containing dosage-form as recited in claim 1, wherein the drug is sodium lithocholoate chenocholate.

162. A drug-containing dosage-form as recited in claim 1, wherein the drug is chenodeoxycholate.

163. A drug-containing dosage-form as recited in claim 1, wherein the drug is ursocholate.

164. A drug-containing dosage-form as recited in claim 1, wherein the drug is ursodeoxycholate.

165. A drug-containing dosage-form as recited in claim 1, wherein the drug is hydrodeoxycholate.

166. A drug-containing dosage-form as recited in claim 1, wherein the drug is dehydrocholate.

167. A drug-containing dosage-form as recited in claim 1, wherein the drug is glycochenocholate.

168. A drug-containing dosage-form as recited in claim 1, wherein the drug is taurochenocholate.

169. A drug-containing dosage-form as recited in claim 1, wherein the drug is taurochenodeoxycholate.

170. A drug-containing dosage-form as recited in claim 1, wherein the drug is sodium lauryl sulfate.

171. A drug-containing dosage-form as recited in claim 1, wherein the drug is salts.

172. A drug-containing dosage-form as recited in claim 1, wherein the drug is alcohol.

173. A drug-containing dosage-form as recited in claim 1, wherein the drug is ethanol.

174. A drug-containing dosage-form as recited in claim 1, wherein the drug is deanol.

175. A drug-containing dosage-form as recited in claim 1, wherein the drug is benzyl alcohol.

176. A drug-containing dosage-form as recited in claim 1, wherein the drug is caffeine.

177. A drug-containing dosage-form as recited in claim 1, wherein the drug is vitamin $B_6$.

178. A drug-containing dosage-form as recited in claim 1, wherein the drug is benzoic acid.

179. A drug-containing dosage-form as recited in claim 1, wherein the drug is laurocapram.

180. A drug-containing dosage-form as recited in claim 1, wherein the drug is 2-hydroxypropyl-β-cyclodextrin.

181. A drug-containing dosage-form as recited in claim 1, wherein the drug is propylene glycol.

182. A drug-containing dosage-form as recited in claim 1, wherein the drug is a buffer.

183. A drug-containing dosage-form as recited in claim 1, wherein the drug is N-methyl pyrrolidone.

184. A drug-containing dosage-form as recited in claim 1, wherein the drug is polyoxyethylene-9-lauryl ether.

185. A drug-containing dosage-form as recited in claim 1, wherein the drug is polyethylene oxide.

186. A drug-containing dosage-form as recited in claim 1, wherein the drug is poleythylene glycol and its derivatives.

187. A drug-containing dosage-form as recited in claim 1, wherein the drug is polyvinyl alcohol.

188. A drug-containing dosage-form as recited in claim 1, wherein the drug is polyvinyl pyrrolidone.

189. A drug-containing dosage-form as recited in claim 1, wherein the drug is a 5-HT agonist.

190. A drug-containing dosage-form as recited in claim 1, wherein the drug is a nonsteroidal anti-inflammatory drug.

191. A drug-containing dosage-form as recited in claim 1, wherein the drug is an antithrombotic.

192. A drug-containing dosage-form as recited in claim 1, wherein the drug is a ganglionic stimulant.

193. A drug-containing dosage-form as recited in claim 1, wherein the drug is an antimuscarinic.

194. A drug-containing dosage-form as recited in claim 1, wherein the drug is a cessation of smoking agent.

195. A drug-containing dosage-form as recited in claim 1, wherein the drug is diprivan.

196. A drug-containing dosage-form as recited in claim 1, wherein the drug is propanolol.

197. A drug-containing dosage-form as recited in claim 1, wherein the drug is bile salt and its derivatives.

198. A drug-containing dosage-form as recited in claim 1, wherein the drug is a fatty acid.

* * * * *